US012616591B1

(12) United States Patent
Major et al.

(10) Patent No.: US 12,616,591 B1
(45) Date of Patent: May 5, 2026

(54) METHOD AND SYSTEM TO MONITOR AND DESIGN PROSTHETICS

(71) Applicants:Northwestern University, Evanston, IL (US); U.S. Govt as rep by the Dept. of Veterans Affairs, Washington, DC (US); Human Motion Technologies LLC, Pittsburg, PA (US)

(72) Inventors: Matthew Justin Major, Chicago, IL (US); Josh Caputo, Pittsburgh, PA (US); Tianyao Chen, Pittsburgh, PA (US)

(73) Assignees: Northwestern University, Evanston, IL (US); U.S. Government as represented by the Department of Veterans Affairs, District of Columbia, WA (US); Human Motion Technologies LLC, Pittsburg, PA (US)

( * ) Notice: Subject to any disclaimer, the term of this patent is extended or adjusted under 35 U.S.C. 154(b) by 775 days.

(21) Appl. No.: 17/958,968

(22) Filed: Oct. 3, 2022

Related U.S. Application Data

(60) Provisional application No. 63/251,771, filed on Oct. 4, 2021.

(51) Int. Cl.
*A61F 2/76* (2006.01)

(52) U.S. Cl.
CPC .......... *A61F 2/76* (2013.01); *A61F 2002/762* (2013.01); *A61F 2002/7635* (2013.01);
(Continued)

(58) Field of Classification Search
CPC .................. A61F 2/76; A61F 2002/762; A61F 2002/7635; A61F 2002/764;
(Continued)

(56) References Cited

U.S. PATENT DOCUMENTS 4,432,223 A * 2/1984 Paquette .................. G01N 3/56
73/73
9,237,935 B2 1/2016 McCloskey et al.
(Continued)

FOREIGN PATENT DOCUMENTS

WO WO 02064068 A1 8/2002
WO WO 2014057086 A1 4/2014
WO WO 2019245981 A1 12/2019

OTHER PUBLICATIONS

Method for carrying out test with test prosthesis for injured leg of patient, involves connecting adapter device to actuator device such that forces and movements are exerted on adapter device to simulate behavior of to-be-tested prosthesis (abstract of DE102012103972A1), Beckerle et al (Year: 2013).*
(Continued)

*Primary Examiner* — Bruce E Snow
(74) *Attorney, Agent, or Firm* — Bell & Manning, LLC

(57) ABSTRACT
An illustrative prosthesis and orthosis testing system includes a platform that receives a prosthesis or orthosis. A motor or a weight are configured to apply a load to the prosthesis or orthosis, and one or more load cells are configured to measure a magnitude of the load on the prosthesis or orthosis. The system also includes one or more encoders configured to measure one or more positions and one or more orientations of the prosthesis or orthosis in response to the applied load.

10 Claims, 12 Drawing Sheets

■ Load cell

● Encoder/Sensors

▨ Pylon

— Cable system

▤ Rail

○ Pulley/roller

▣ Electric motor

▭ Linear actuator

▊ Linear bushing

(52) U.S. Cl.
CPC . *A61F 2002/764* (2013.01); *A61F 2002/7645*
(2013.01); *A61F 2002/7695* (2013.01)

(58) Field of Classification Search
CPC ..... A61F 2002/7645; A61F 2002/7695; A61B
5/6811; A61B 5/6812; A61B 5/6828;
A61B 5/6829
See application file for complete search history.

(56) References Cited

U.S. PATENT DOCUMENTS

| | | | |
|---|---|---|---|
| 2014/0076029 A1 | 3/2014 | Lee | |
| 2019/0350729 A1 | 11/2019 | Prost et al. | |
| 2021/0015641 A1* | 1/2021 | Mahon | A61F 2/5046 |
| 2022/0387196 A1* | 12/2022 | Westgard | A61F 2/76 |
| 2023/0095380 A1* | 3/2023 | Yalla | G01N 3/06 |
| | | | 73/818 |

OTHER PUBLICATIONS

M. Cempini, L. J. Hargrove and T. Lenzi, "Design, development, and bench-top testing of a powered polycentric ankle prosthesis," 2017 IEEE/RSJ International Conference on Intelligent Robots and Systems (IROS), Sep. 2017, pp. 1064-1069, doi: 10.1109/IROS. 2017.8202276: Fig 4.

T. Elery, S. Rezazadeh, C. Nesler, J. Doan, H. Zhu and R. D. Gregg, "Design and Benchtop Validation of a Powered Knee-Ankle Prosthesis with High-Torque, Low-Impedance Actuators," 2018 IEEE International Conference on Robotics and Automation (ICRA), May 2018, pp. 2788-2795, doi: 10.1109/ICRA.2018.8461259.

* cited by examiner

Manufacturing Aim: Measure device function for quality control and ensure they satisfy functional requirements as designed Manufacture commercial device Record mechanical function and perform quality control

METHOD AND SYSTEM TO MONITOR AND DESIGN PROSTHETICS

CROSS-REFERENCE TO RELATED APPLICATION

The present application claims the priority benefit of U.S. Provisional Patent App. No. 63/251,771 filed on Oct. 4, 2021, the entire disclosure of which is incorporated by reference herein.

BACKGROUND

A prosthesis refers generally to any type of artificial body part, such as a limb, a heart, an implant, etc. For individuals with limb loss (e.g., arm loss or leg loss), prosthetics manufacturers produce various modular prosthetic components that can be used to help improve quality of life. These components come in different shapes, sizes, and stiffness levels, and are generally prescribed to patients based on their stature, weight, and activity level. However the mechanical function and properties of these devices are not disclosed by manufacturers, leaving researchers and clinicians in the dark regarding information on how each device performs compared to others, and manufacturer quality control.

SUMMARY

An illustrative prosthesis and orthosis testing system includes a platform that receives a prosthesis or orthosis and a motor or a weight configured to apply a load to the prosthesis or orthosis through a pylon. The system also includes one or more load cells configured to measure a magnitude of the load on the prosthesis or orthosis. The system further includes one or more encoders configured to measure one or more positions and one or more orientations of the prosthesis or orthosis in response to the applied load.

In an illustrative embodiment, the system includes a linear actuator attached to the platform, and the motor is configured to manipulate the linear actuator to move the pylon. The system can also include an accelerometer configured to measure an acceleration of the prosthesis or orthosis in response to the applied load. In one embodiment, the one or more load cells comprise an integrated 3-axis load cell. In some embodiments, the one or more encoders comprise one or more linear encoders and one or more rotational encoders.

In another embodiment, the one or more encoders are configured to calculate a deformation of the prosthesis or orthosis based on the one or more positions and the one or more orientations of the prosthesis or orthosis. A characteristic of the prosthesis or orthosis can be determined based on the deformation. In another embodiment, the system includes a processor in communication with the one or more encoders, where the processor is configured to determine a center of pressure location on the prosthesis or orthosis based at least in part on data from the one or more encoders. In another embodiment, the pylon is attached to the platform, and the prosthesis or orthosis is mounted to the pylon. In yet another embodiment, the load applied to the prosthesis or orthosis is controlled such that the prosthesis or orthosis deforms without over constraint.

In some embodiments, the system further includes a processor in communication with the one or more encoders, where the processor is configured to determine a roll-over shape of the prosthesis or orthosis based at least in part on the data from the one or more encoders. In another embodiment, the processor is configured to determine a torque-ankle curve of the prosthesis or orthosis based at least in part on the data from the one or more encoders. In some embodiments, the motor or the weight moves the pylon through a range of angles under the load. In other embodiments, the pylon is constrained at a fixed angle such that the load is axially applied to the pylon by the motor or the weight.

An illustrative method of testing a prosthesis or orthosis includes applying, by a motor or a weight that applies force to a pylon, a load to a prosthesis or orthosis that is mounted to the pylon. The method also includes measuring, by one or more load cells or one or more strain gauges, a magnitude of the load on the prosthesis or orthosis. The method also includes measuring, by one or more encoders, one or more positions and one or more orientations of the prosthesis or orthosis in response to the applied load. The method further includes determining, by a processor in communication with the one or more encoders and the one or more load cells or strain gauges, a characteristic of the prosthesis or orthosis based at least in part on the one or more positions and the one or more orientations of the prosthesis or orthosis.

In one embodiment, applying the load comprises applying the load through a range of angles of the pylon. In another embodiment, applying the load comprises applying the load at a fixed angle such that the load is axially applied to the pylon. The method can also include determining, by the processor, a roll-over shape of the prosthesis or orthosis based at least in part on the data from the one or more encoders. The method can also include determining, by the processor, a torque-ankle curve of the prosthesis or orthosis based at least in part on the data from the one or more encoders. The method can further include determining, by the processor, a center of pressure location on the prosthesis or orthosis based at least in part on data from the one or more encoders. The method can further include measuring, by an accelerometer, an acceleration of the prosthesis or orthosis in response to the applied load.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1A:
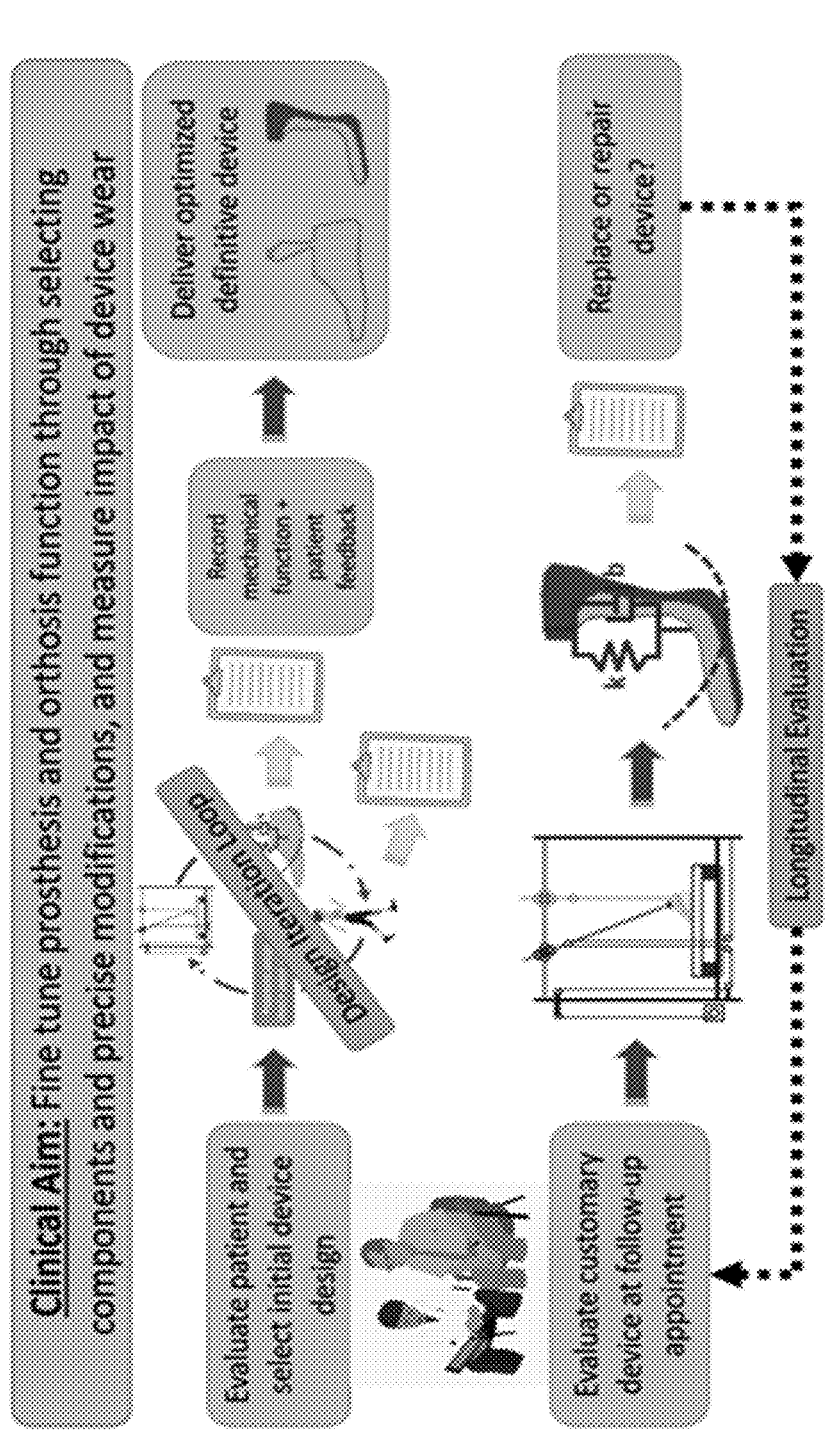
FIG. 1A depicts integration of the proposed system into the clinical sector in accordance with an illustrative embodiment.

The World Health Organization (WHO) estimates that there are more than 30 million people worldwide with health presentations that can be addressed through the use of orthotic and prosthetic (O&P) devices. In the United States, nearly 59% of orthotic patient encounters and 90% of prosthetic patient encounters are related to the lower limbs, thereby representing the vast majority of delivered device interventions. The delivery of these interventions are intended to support functional mobility and independence of patient groups with relevant pathology, including limb loss and chronic stroke, and have proven to significantly lower healthcare costs associated with treating these conditions. Importantly, the observed reduction in costs compared to matched Medicare beneficiaries who did not receive these interventions were reflected by lower care expenses in orthosis users despite more therapy and lower hospital rates for prosthesis users, suggesting value to both patients and payers.

To address O&P clinical needs, there are 13 accredited clinical education programs in the United States that award a Masters in Prosthetics and Orthotics, and approximately 24 schools worldwide that provide high-level training to students on how to assess patients and design custom O&P device interventions. Inherent to the clinical practice of delivering a definitive prosthesis and orthosis is the custom design of these devices that accounts for a user's unique impairments and needs. Individuals who benefit from using prostheses and orthoses belong to a highly heterogeneous cohort, with each individual presenting their own physical characteristics, functional abilities, and desires. These person-specific qualities must be considered when delivering a device to ensure a patient's long-term rehabilitation success while accounting for changes in their functional status. As part of their clinical education, students must master the skill of performing careful design iterations of these custom device interventions to ensure that they support a patient's attainment of their full rehabilitation potential and can adapt to their changing presentation.

As lower limb O&P care is device driven, the design process of lower limb O&P devices should be rigorous, and is a function of adjusting their mechanical function, which is defined by their physical properties of the device including stiffness, damping, and roll-over geometry. Although different design features dictate the mechanical function of a leg prosthesis or ankle-foot orthoses (AFOs), this function drives user response by interacting with intact anatomy and therefore patient rehabilitation outcomes.

In the case of a transtibial prosthesis user, prosthetists assemble the device from a selection of commercial modular ankle-foot components that are attached to a socket serving as the residuum-prosthesis interface. The features of these components can vary considerably, can be designed with different shapes, and can come in sizes and stiffness/damping properties that are prescribed to patients based on their stature, weight, and activity level. While there are certain standards to regulate the safety of these devices, such as International Standards Organization (ISO) 10328 and 22675, the inherent mechanical function and properties of these devices are not disclosed by manufacturers. Consequently, prosthetists routinely rely on device classifications (e.g., solid ankle-cushioned heel, single-axis, dynamic response) and manufacture-recommended settings (stiffness, dimensions) to optimize the prosthetic setup. This selection process also operates on the assumption that prosthesis manufacturers are exercising strict quality control procedures, such that gradients of stiffness (low, medium, high) are accurate and reliable to allow selection for an individual user.

Recent investigations have provided strong evidence that the mechanical properties of a transtibial prosthesis (heel/keel stiffness/damping, pylon stiffness) can influence clinically-relevant performance outcomes, including stability, metabolic cost, and residual limb loading, and small differences in these properties can be detected by the user. Importantly, the mechanical properties of prostheses will degrade due to environmental exposure, which will in turn affect user performance. Furthermore, while prosthetists clinically optimize the prosthetic setup according to the rigorously designed mechanical function of the assembled components, they have little control over the types of footwear used with these devices, which can drastically affect prosthesis properties.

In the case of an AFO user, orthotists custom fabricate the orthotic interface from raw materials (thermoplastics) to intimately match the anatomy of the user and design the mechanical function of the device through modifications to the orthosis shell (corrugations, thickness) and/or addition of prefabricated joints. Similar to prostheses, AFO mechanical design is critical to addressing user needs and highly dependent on the type of foot and ankle joint support recommended for their specific impairment, such as muscle weakness, motor control deficits, spasticity, instability, and/or balance problems due to pathologies such as chronic stroke cerebral palsy. The amount of ankle joint resistance delivered by an AFO can affect multiple performance outcomes (e.g., lower extremity joint motion, muscle activity, metabolic cost, ground reaction forces, and spatiotemporal parameters).

Footwear can also have a profound influence on the mechanical function of an AFO. However, unlike prostheses that can be assembled from standard commercial components, the custom modifications applied to orthotic design can theoretically yield an infinite number of mechanical properties that are not typically measured in the clinic. Orthotists must rely on their skill and experience to optimize device design through careful selection of materials and subsequent modifications. Although not clinically recommended, users of orthotic devices can also select to use prefabricated components, but their mechanical function is typically unknown to both the user and a prescribing clinician. Furthermore, the issue of unknown mechanical function also applies to 3D printed orthotic devices, in which the resulting device needs to be mechanically characterized to verify that it satisfies its design parameters.

Thus, while the mechanical function of transtibial prostheses and AFOs are intimately tied to the rehabilitation outcomes of the device user, there is no standardized method to capture these mechanical properties, and accessibility to mechanical testing systems for educators, clinicians, researchers, and some manufacturers is limited due to the cost and/or bespoke nature of these systems. Historically, industrial materials testing systems have been retrofit to perform prosthesis mechanical characterization, or experimental devices have been custom built in research settings. Similarly, low-tech systems have been developed to measure AFO stiffness that could in theory be implemented in clinical environments. However, these approaches are bespoke and/ or often expensive if material test systems are used, and may require technical expertise, thereby limiting their applicability, accessibility, and global utility. Without a valid, standardized means to measure mechanical properties of O&P devices, it is near impossible to communicate this information globally between research laboratories, clinics, and clinical/engineering education programs. A lack of standardization is particularly detrimental to rehabilitation research that relies on consistent, accurate, and reliable information for defining the relationships between device properties and user outcomes to inform clinical practice guidelines.

Bench test designs have been proposed by O&P professional organizations to standardize measurement and facilitate communication, but these tests still rely on retrofitting industrial testing systems. The WHO International Classification of Functioning, Disability and Health created a standardized language to define and communicate functional disability with the purpose of elevating global evidence-based care, and such a language is very important to communicate mechanical function of O&P devices to satisfy the same purpose. To this end, ISO has now started to develop a standard for measuring, quantifying, and reporting mechanical characteristics of lower limb prosthetic components (ISO/TS 16955: Prosthetics—Quantification of physical parameters of ankle foot devices and foot units).

Described herein are methods and systems that provide a universal way to characterize the mechanical function of lower limb O&P components in clinics, research, and educational settings. The proposed methods and systems provide the first available tool to characterize the mechanical function of O&P components that is widely accessible due to its minimal size and relative cost. Knowledge of prosthesis and orthosis mechanical function will aid prescription guidelines for improved patient quality of life, interpretation and design of prosthesis and orthosis comparative research, and instruction of rehabilitation science in clinical/engineering educational courses.

Given that the mechanical function (stiffness, damping, roll-over geometry, etc.) is inherent to the custom design of lower extremity O&P devices and is tuned to address specific patient needs, one core innovation of the proposed system is to grant access to bench testing professionals in each foundational sector of the O&P industry (clinical, education, research, and industry). This goal can be achieved by developing a more economical way to deliver standardized, quantitative information on lower limb O&P device mechanical properties. In some embodiments, the proposed technology does not measure human subject information, but rather patient-independent bench test information on any transtibial prosthetic component or AFO across gender, age, and pathology. Currently, bench tests systems for these devices only exist to perform ISO testing for safety and durability (ISO 10328, 22675) but not performance-related characterization, and those systems cost between $145,000 and $190,000.

Compared to these existing systems and techniques, the proposed system innovates in several ways: 1) the proposed system is a first-of-kind with no known competitor that addresses the market gap; 2) the system is designed for O&P professionals and students with fully packaged hardware-software that eliminates the need for bespoke solutions; 3) the materials sourcing suggests the system will be affordable at a price point of ~$10,000; 4) the proposed design is suitable for benchtop use for easy deployment in clinics; and 5) the system outcomes will provide a common language framework of O&P device mechanical function that is relevant to educators, scientists, clinicians, and manufacturers. Importantly, the proposed system also offers complementary information to each O&P sector and will not replace existing practices, but will instead support them with objective data. Additionally, while the systems described herein are illustrated with reference to the testing of prosthetics and orthotics, it is to be understood that the proposed systems are not so limited. For example, any of the proposed systems can be used to test any type of footwear, such as shoes, sandals, boots, athletic equipment, etc.

FIG. 1 illustrates the envisioned integration of the proposed system into each O&P sector. Specifically, FIG. 1A depicts integration of the proposed system into the clinical sector in accordance with an illustrative embodiment. FIG. 1B depicts integration of the proposed system into the education sector in accordance with an illustrative embodiment. FIG. 1C depicts integration of the proposed system into the research sector in accordance with an illustrative embodiment. FIG. 1D depicts integration of the proposed system into the manufacturing sector in accordance with an illustrative embodiment.

Figure 1B:
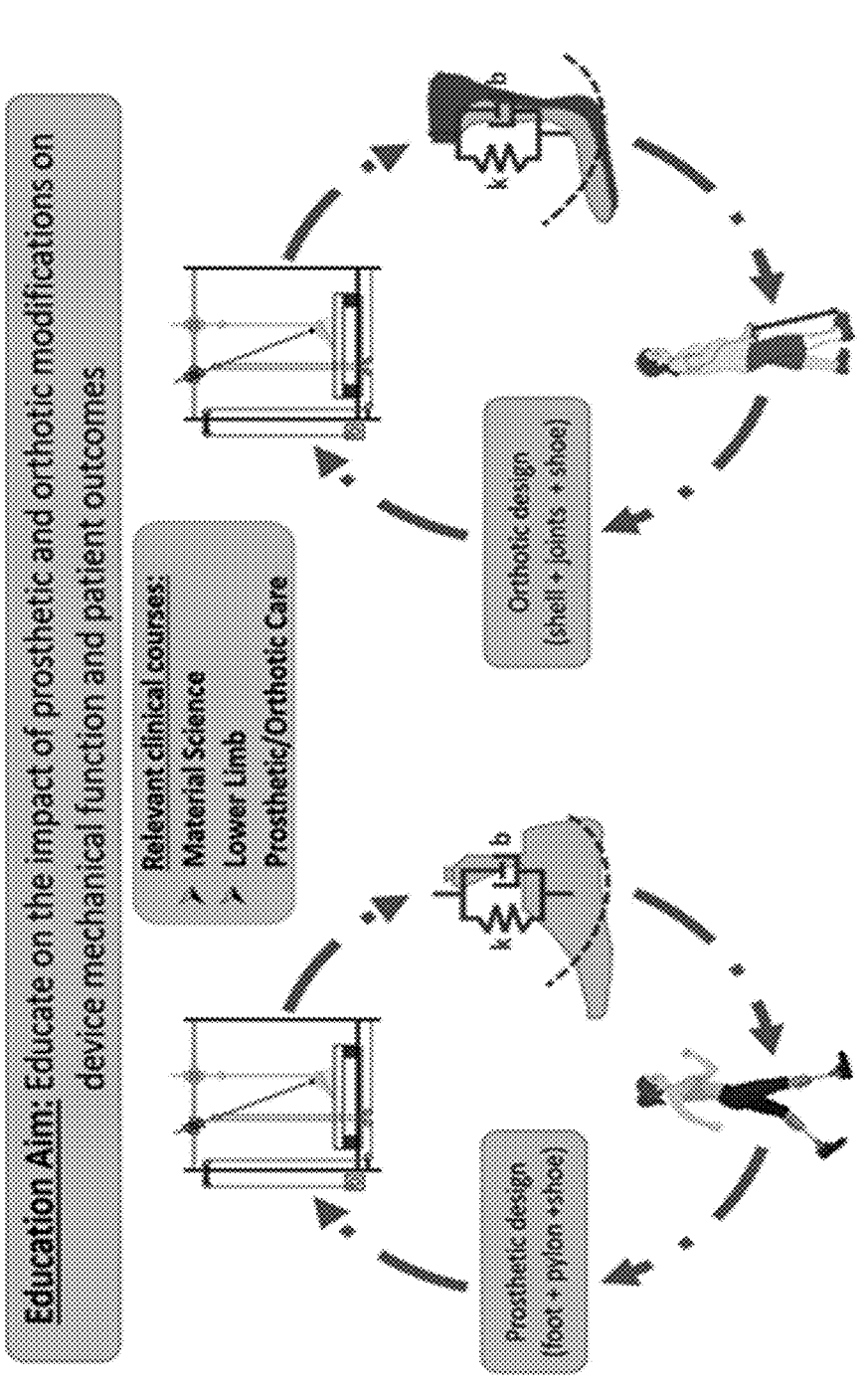
FIG. 1B depicts integration of the proposed system into the education sector in accordance with an illustrative embodiment.

In FIG. 1A, the clinical aim is to fine tune prosthesis and orthosis function through selecting components and precise modifications, and by measuring the impact of device wear. Operations involved to perform this clinical aim include an initial patient evaluation and selection of a device design, followed by a design iteration loop. Mechanical function and patient feedback are recorded during the design process such that an optimized definitive device is delivered to the patient. FIG. 1A also shows evaluation of the device at a follow-up appointment to determine whether device repair or replacement is needed. As shown in FIG. 1B, the educational aim is to educate individuals on the impact of prosthetic and orthotic modifications on device mechanical function and patient outcomes. As shown in FIGS. 1A and 1B, clinicians and students will be able measure the effects of their modifications on O&P device function to fine tune the definitive system, and clinicians will be able to measure the effects of long-term use and potential damage to devices that affect function.

Figure 1C:
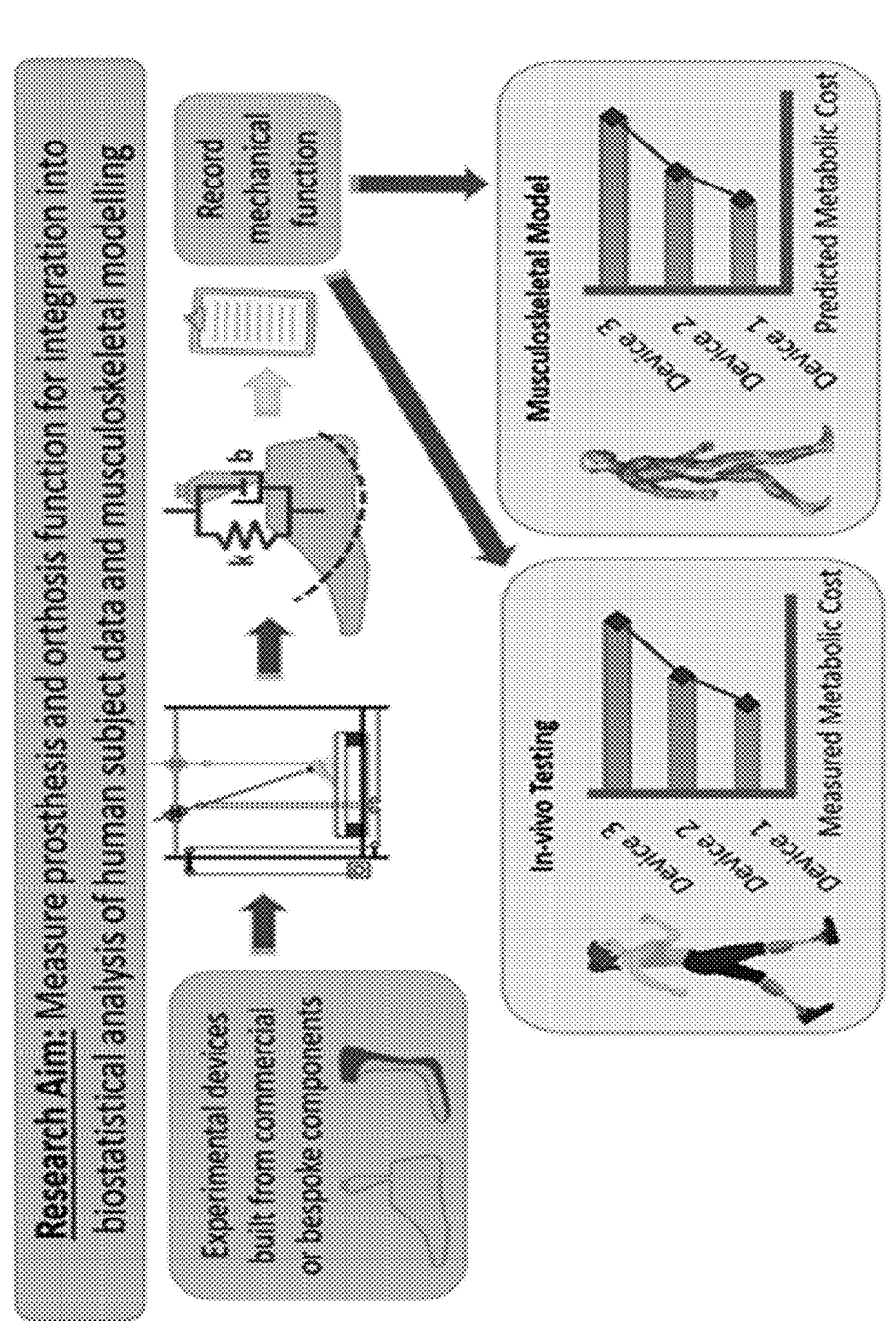
FIG. 1C depicts integration of the proposed system into the research sector in accordance with an illustrative embodiment.

In FIG. 1C, the research aim is to measure prosthesis and orthosis function for integration into biostatistical analysis of human subject data and musculoskeletal modelling. FIG.

Figure 1D:
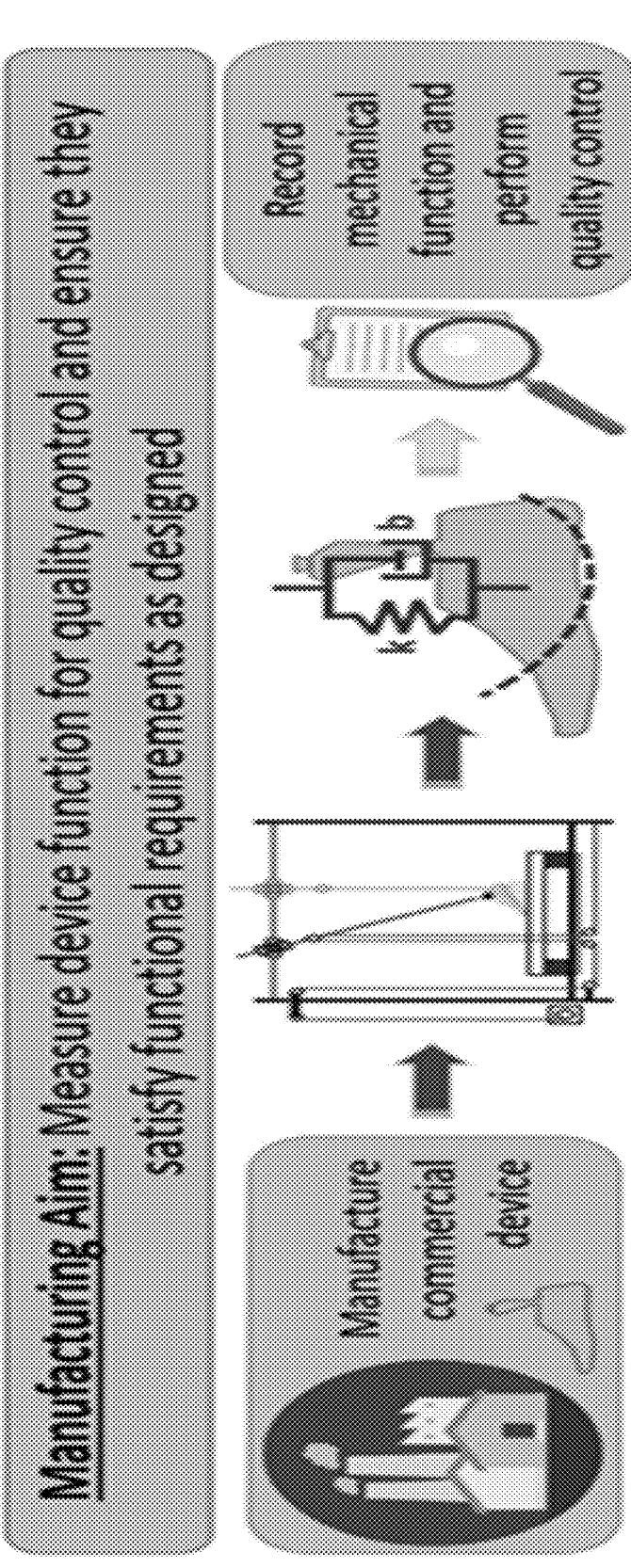
FIG. 1D depicts integration of the proposed system into the manufacturing sector in accordance with an illustrative embodiment.

1C shows how researchers will be able measure device function to characterize relationships between mechanical properties and user outcomes for optimizing design and prescription guidelines. Additionally, in accordance with the manufacturing aim, industry manufacturers will be able to measure device properties of fabricated components to ensure quality control, as shown in FIG. 1D.

To help assess the state of the art of prosthetics testing, data of prosthesis foot testing in the sagittal plane was collected using an R-2000 Rotopod (Parallel Robotics System Corporation; Hampton, NH) robot gait system. Testing results suggest that the measured stiffness of prosthesis devices are largely inconsistent with the manufacture-claimed stiffness, and further supports the importance of independent device testing. Also used was a sophisticated mechatronic platform that allows prosthesis users to walk with a robotic ankle-foot prostheses that can rapidly adjust its keel stiffness on command.

Figure 2B:
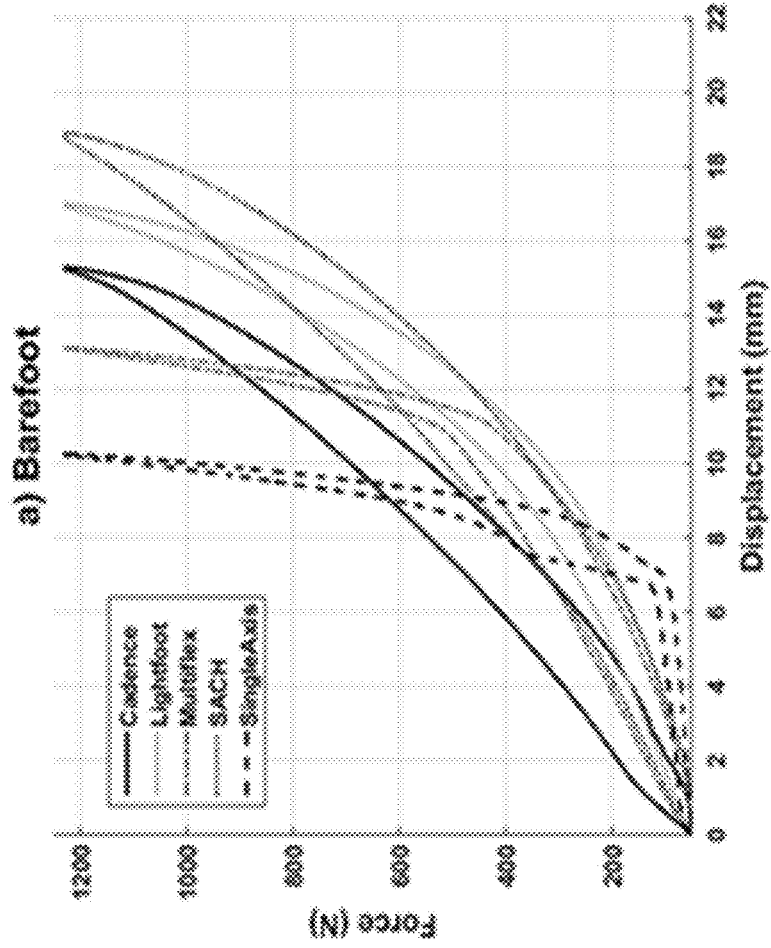
FIG. 2B depicts test results for five feet in the form of force displacement data in accordance with an illustrative embodiment.
Figure 2A:
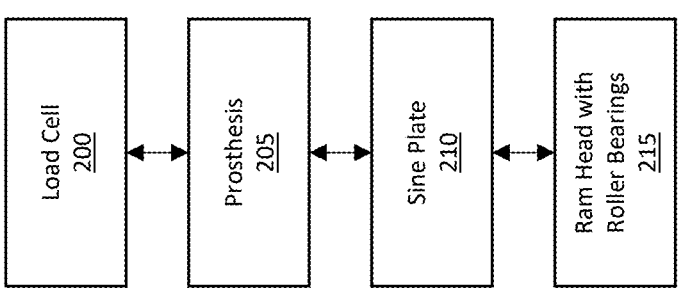
FIG. 2A is a block diagram of a universal testing machine in accordance with an illustrative embodiment.

In parallel with the system design, mechanical characterization was performed on O&P devices. For prostheses, force-displacement data was captured for four different prosthetic foot design types (solid-ankle cushioned heel, single-axis, multi-axial, and dynamic response) at the heel, keel, and mid-stance orientations using a universal materials test machine and according to established protocols. FIG. 2A is a block diagram of a universal testing machine in accordance with an illustrative embodiment. As shown, the universal testing machine includes a load cell 200 with a prosthesis 205 mounted thereto, a sine plate 210, and a ram head with roller bearings 215. FIG. 2B depicts test results for five feet in the form of force displacement data in accordance with an illustrative embodiment.

Figures 3A, 3B:
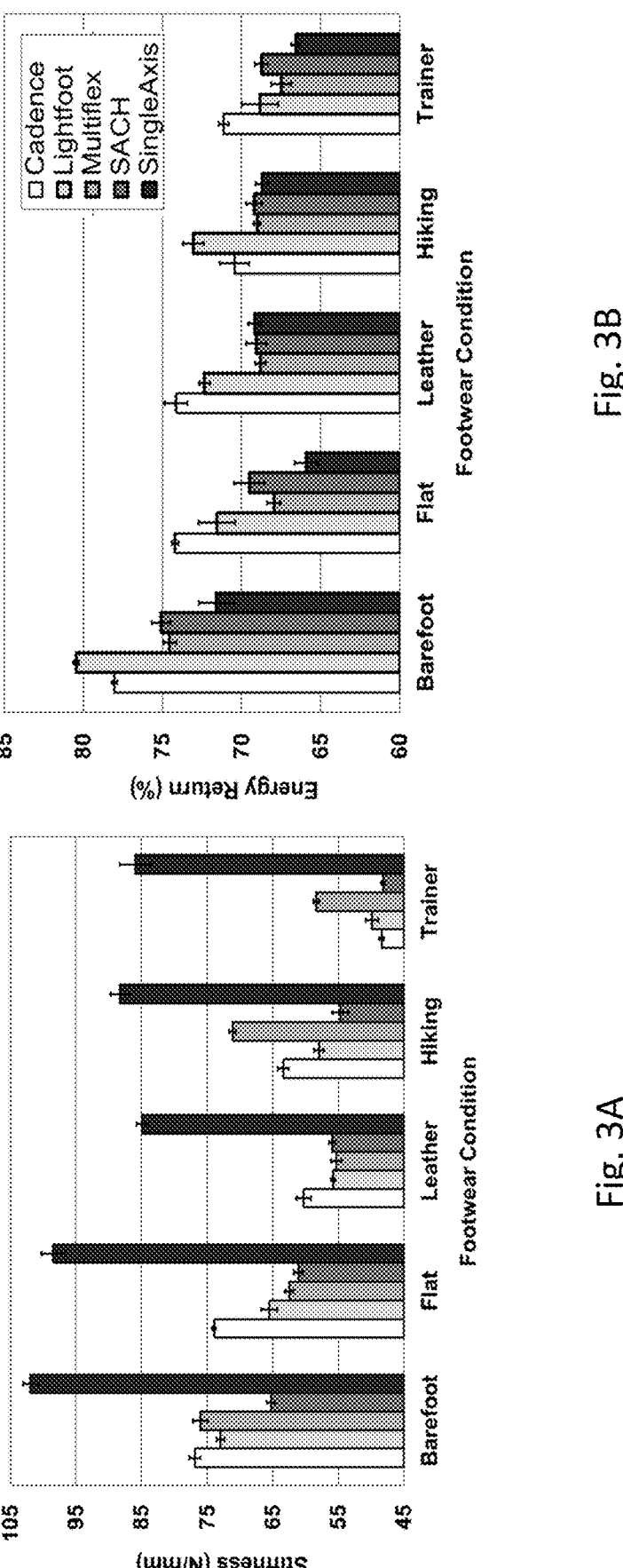
FIG. 3A depicts the results of a stiffness test for five prosthetic feet while wearing different shoes in accordance with an illustrative embodiment.
FIG. 3B depicts the results of an energy return test for five prosthetic feet while wearing different shoes in accordance with an illustrative embodiment.

The present design team has extensive experience designing and evaluating bench test protocols to characterize O&P devices, and this preliminary work has laid the groundwork for the proposed design. Over the past several years, work has focused development of new standardized methods for characterizing the mechanical function of prostheses and assessing differences in properties between designs and the effects of footwear on those properties. In particular, the designers have worked with the American Orthotic and Prosthetic Association to evaluate the validity and reliability of proposed standardized bench test methods to categorize transtibial prosthetic components. These bench test methods utilize universal materials test systems to measure force-displacement while compressing prosthetic feet at different orientations to estimate stiffness and energy return of these devices. FIG. 3A depicts the results of a stiffness test for five prosthetic feet while wearing different shoes in accordance with an illustrative embodiment. FIG. 3B depicts the results of an energy return test for five prosthetic feet while wearing different shoes in accordance with an illustrative embodiment. It is noted that the results shown in FIGS. 3A and 3B were obtained using the universal testing machine depicted in FIG. 2A.

Importantly, it was determined there is no standardized methodology for characterizing prosthesis mechanical function, and the designers turned early on to the development of standardized bench test methods and language for comprehensively describing the mechanical properties of transtibial prosthetic systems. The intention of that early work was to create a universal characterization method to incorporate information on the mechanical function of prostheses, rather than ambiguous and non-descriptive prosthesis trade names and classifications, in prosthetics research. These methods involved simple, low-cost and instrumented apparatuses which inform the designs (e.g., inverted pendulum, load cells, etc.) of the proposed system.

Figures 4A, 4B:
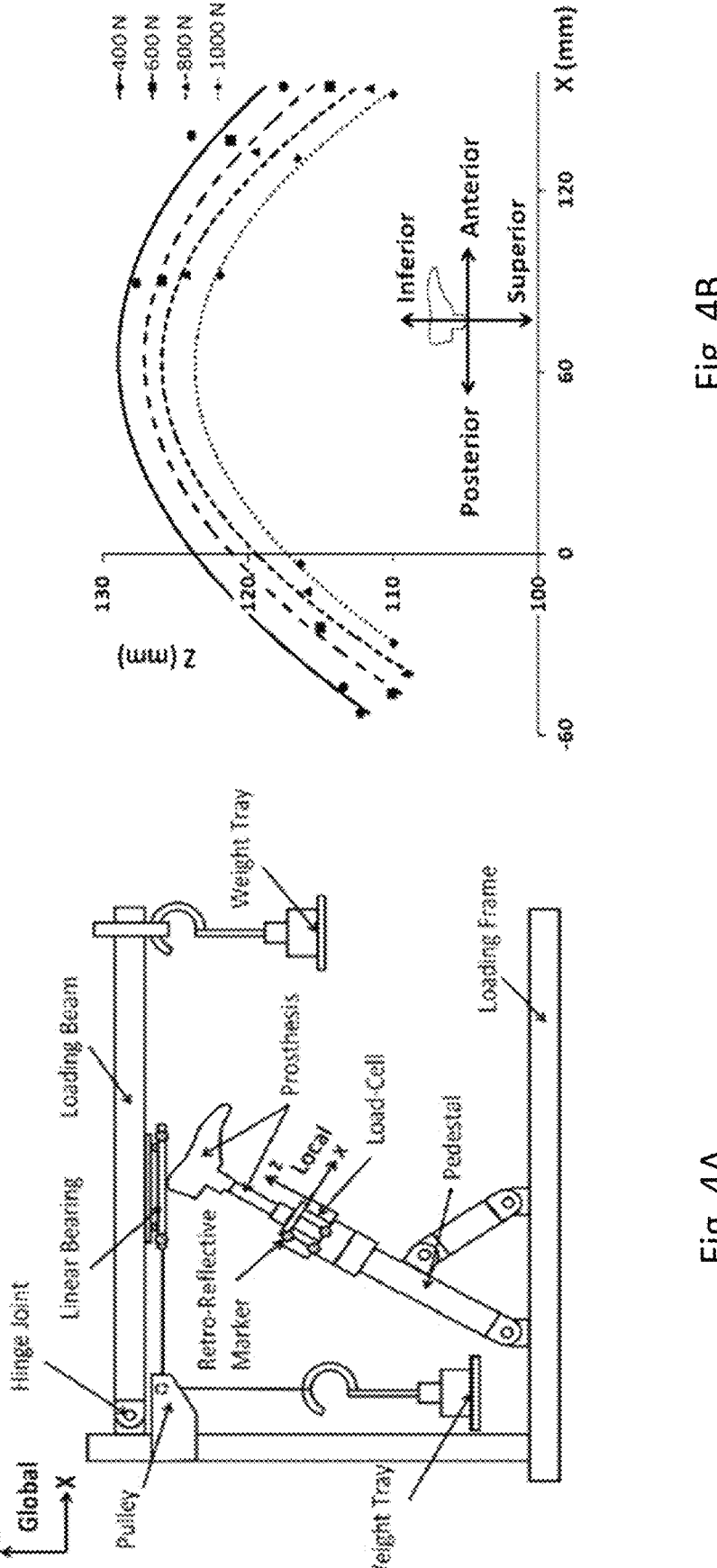
FIG. 4A depicts a cantilever bench test system in accordance with an illustrative embodiment.
FIG. 4B depicts standardized measurement of mechanical properties of a transtibial prosthesis tested using the proposed system in accordance with an illustrative embodiment.

FIG. 4A depicts a cantilever bench test system in accordance with an illustrative embodiment. As shown, the test system includes a loading frame, an adjustable pedestal mounted to the loading frame, a load cell mounted to the adjustable pedestal and having retroreflective markers attached thereto, and a prosthesis attached to the load cell. In some embodiments, strain gauge(s) (i.e., sensors with a measured electrical resistance that varies with applied force) can be used instead of or in combination with the load cell(s). Also included are a first weight tray connected to a pulley, a hinge joint, a linear bearing, a loading beam, and a second weight tray attached to the loading beam. In an illustrative embodiment, the first weight tray and pulley system is used to apply a shear (horizontal) force through the linear bearing at the loaded region of the prosthetic foot. The second weight tray is used to apply a normal (vertical) force at the loaded region of the prosthetic foot. Position of the retroreflective markers are tracked with a digital camera-based optical motion capture system to record three-dimensional position of the prosthesis to estimate plantar center of pressure relative to a local prosthesis-based reference frame. Combining simultaneous measurement of the marker positions and load cell forces and moments during loaded and unloaded conditions, foot deformation and shear and normal stiffness can be estimated. Loading the second weight tray and initiating an oscillation of the loading beam by pulling down and releasing the weight tray allows for estimation of damping at the loaded region of the prosthetic foot. These measurements of displacement, stiffness, and damping can be recorded for different prosthesis orientations by adjusting the pedestal orientation. Multiple measurements across different prosthesis orientations are used to create roll-over curves and multiple loading conditions can be used to create a 'family' of roll-over curves. FIG. 4B depicts standardized measurement of mechanical properties of a transtibial prosthesis tested using the proposed system in accordance with an illustrative embodiment. Specifically, shown is a family of roll-over curves resulting from different applied weights.

Figure 4D:
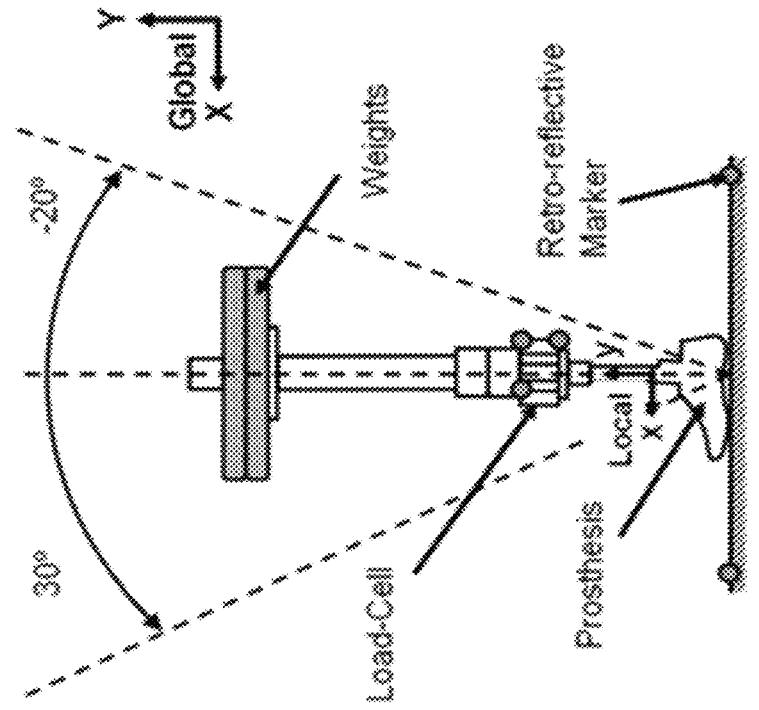
FIG. 4D depicts an instrumented inverted pendulum testing apparatus in accordance with an illustrative embodiment.
Figure 4C:
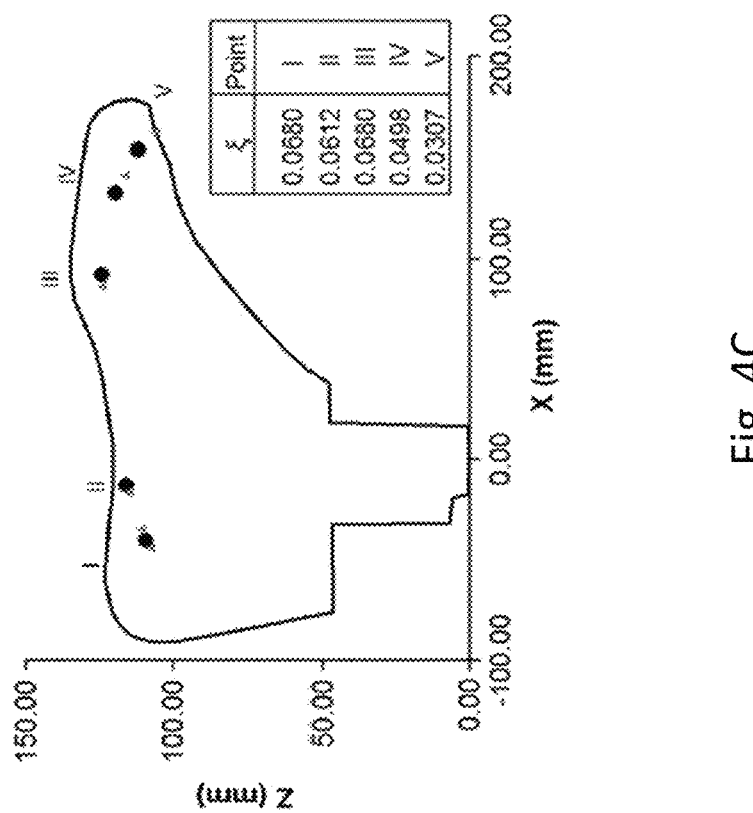
FIG. 4C depicts normal deflection, shear deflection, and damping coefficient test results in accordance with an illustrative embodiment.

FIG. 4C depicts normal deflection, shear deflection, and damping coefficient test results in accordance with an illustrative embodiment. FIG. 4D depicts an instrumented inverted pendulum testing apparatus in accordance with an illustrative embodiment. The apparatus of FIG. 4D includes a prosthesis mounted to a load cell, and weights applied to the load cell. Additionally, one or more retroreflective markers is used on the test surface upon which the prosthesis is placed. In some embodiments, the proposed system can include both a cantilever bench test (FIG. 4A) and an inverted pendulum bench test (FIG. 4D) to maximize the types of tests that can be performed. In an illustrative embodiment, the bench test systems will apply loads to a prosthetic component through a translatable platform, the position of which is controlled through a lead screw and motor in some embodiments. The linear position of the platform is measured with linear transducers. The applied load magnitude is measured with an integrated 3-axis load cell, and the applied load acceleration is measured with an accelerometer. The position of the prosthetic component is measured through rotational and linear transducers.

Discussed below is the design and fabrication of the testing system for mechanical characterization of prosthetic foot-ankle mechanisms and ankle-foot orthoses (AFO). In alternative embodiments, the system can be used to test other lower limb and/or upper limb prosthetics. The goal of the design was to develop a mechanical testing system that 1) loads the testing sample in a realistic way and automatically analyzes and presents the result; 2) is relatively low cost compared to current testing machines; and 3) has dimensions and weight that are suitable for benchtop use. Existing testing machines constrain the deformation of the foot during loading, which may result in inaccurate measurement. In an illustrative embodiment, the proposed system is designed to be under-constrained, eliminating something unnatural from happening. The system will be able to output the following types of measurements: family of roll-over curves, rotational stiffness at the joint (torque-angle curve), and linear damping and stiffness at different orientations including the heel, toe, and mid-stance, respectively, etc. To generate these outputs, a prosthesis or orthosis is attached to the system and undergoes loading and unloading at different orientations, either through manual or actuated manipulation. The system records and processes measurement of the prosthesis or orthosis position, deformation, and applied load to estimate outputs and report these outputs. For example, roll-over curves are generated from measuring data while loading the prosthesis or orthosis through continuous changes in its orientation, and stiffness and damping estimates are generated from measuring data while loading and unloading the prosthesis or orthosis at a single orientation but can be estimated independently for all the orientations used to produce the roll-over curves.

Figures 5A, 5B:
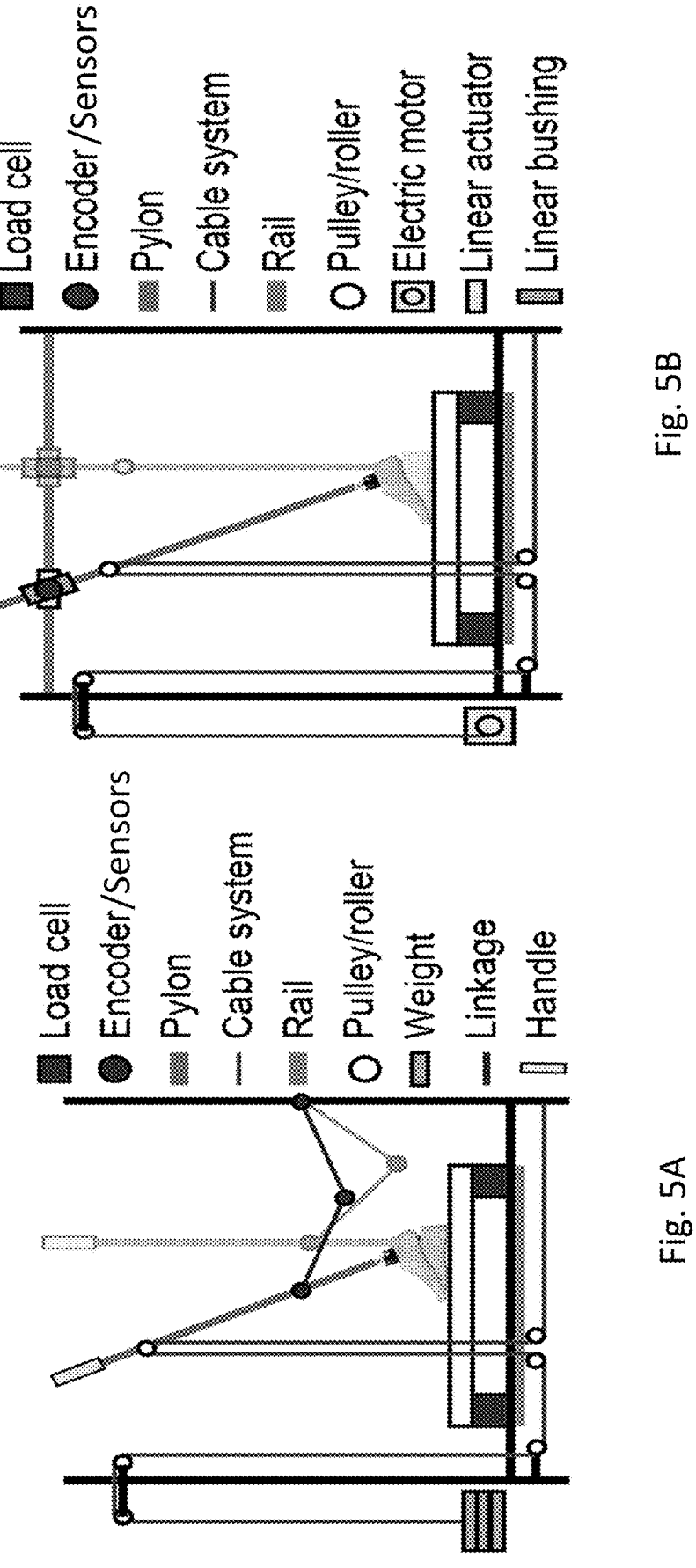
FIG. 5A depicts a passive manual testing system in accordance with an illustrative embodiment.
FIG. 5B depicts an actuated testing system in accordance with an illustrative embodiment.
Figure 5C:
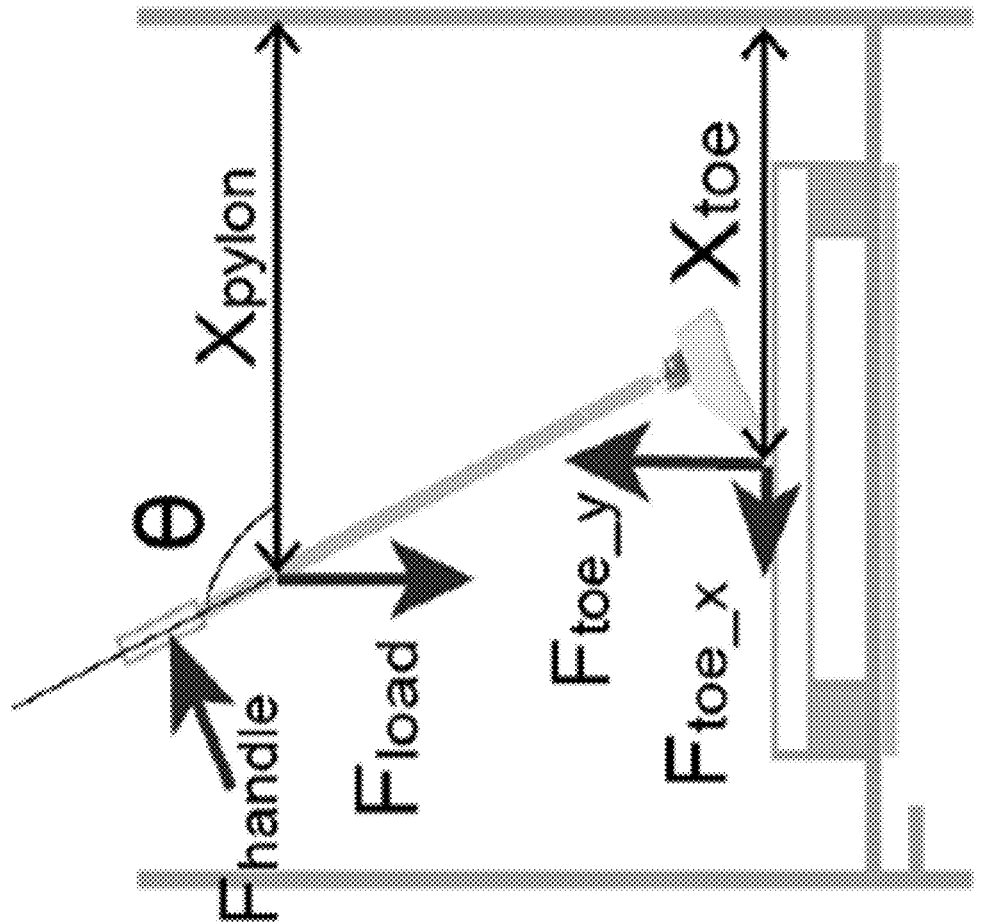
FIG. 5C is a pylon kinematics diagram ($\theta$, $X_{pylon}$) for solving free body diagram unknowns in accordance with an illustrative embodiment.

As discussed above, at least some embodiments of the system incorporate an inverted pendulum model into the system design. This model allows the center of pressure (COP) to travel forward along the curved foot. In some embodiments, the system can include two different subsystems that operate with either manual or actuated control, as shown in FIG. 5. FIG. 5A depicts a passive manual testing system in accordance with an illustrative embodiment. FIG. 5B depicts an actuated testing system in accordance with an illustrative embodiment. In the embodiment of FIG. 5A, the testing sample is loaded via a cable loading system, which is displayed in part. In the embodiment of FIG. 5B, the testing sample is loaded by motors which power the system. The systems of FIGS. 5A and 5B include various components, such as a load cell, encoder/sensors (e.g., accelerometer), pylon, cable system, rail, pulley/roller, weight or an electric motor, a linkage or linear actuator, and a handle or linear bushing. In alternative embodiments, the systems of FIGS. 5A and 5B may include fewer, additional, and/or different components. During operation, the prosthesis or orthosis is attached to the system pylon and either loaded and unloaded with weights and moved through different orientations via manual manipulation of the handle as in the passive manual testing system, or automatically loaded and unloaded and moved through different orientations via actuators and electric motors as in the actuated testing system. In both embodiments, data is captured with the sensors, encoders, and load cell to process data and generate outputs. FIG. 5C is a pylon kinematics diagram ($\theta$, $X_{pylon}$) for solving free body diagram unknowns in accordance with an illustrative embodiment. The pylon kinematics are available via encoder data, and the COP locations ($X_{toe\_x}$, $F_{toe\_y}$) are calculated from the encoder data.

An advantage of a manual system is ease in developing these types of systems to guarantee its development, and this method will lower cost, as it does not involve actuation through motors. The actuated system will minimize human error during testing but would be more expensive as the motion is automated through motors and linear actuators. Dynamics of both systems are the same for standardization. The operator will manually move the pylon as guided by an auditory cue to a set rotational speed for the manual system, while the procedure will be automated based on initial inputs for the actuated system. Two load cells will measure the load magnitude and COP, and encoders on the linkage will accurately calculate the test sample position, orientation, and deformation. A cable loading system with a 4:1 force amplification applies load to the pylon in the direction of gravity. Alternatively, a different force amplification ratio may be used such as 3:1, 5:1, etc. Test results can be visualized through a graphical user interface (GUI) that will report key parameters such as roll-over shape and torque-ankle curve. The GUI will empower the users to make comparisons with various foot data in a user-generated database. The development of the GUI can be refined according to feedback from the validity and reliability assessments of the system.

Figure 6:
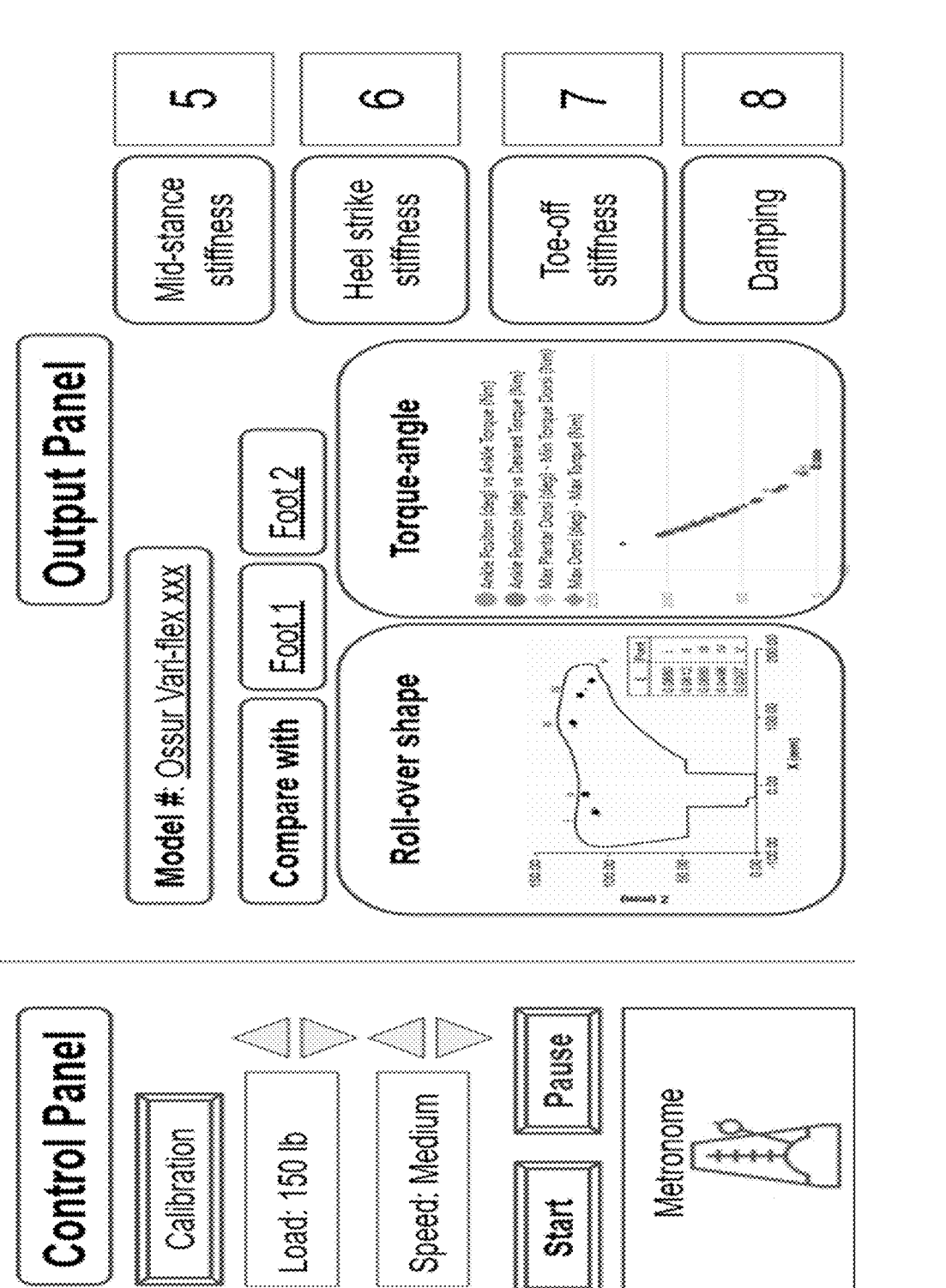
FIG. 6 depicts a graphical user interface of the system in accordance with an illustrative embodiment.

FIG. 6 depicts a graphical user interface of the system in accordance with an illustrative embodiment. As shown, the GUI includes a control panel and an output panel. The control panel includes a calibration instruction to perform system calibration, a desired load, a desired speed, a start test button, a pause test button, etc. The output panel displays test results such as mid-stance stiffness, heel strike stiffness, toe-off stiffness, and damping. The output panel also includes data regarding roll-over shape and torque angle for the prosthesis or orthosis. Additionally, the output panel allows the user to compare different prosthetic or orthotic devices.

The test protocol for the system follows established procedures based on prior research and analysis. The system will either guide users (manual control) or automatically (actuated control) move the pylon angle $\theta$ (FIG. 5C) through the following positions: 73°, 81°, 90° (shank vertical), 110°, and 124° to simulate stance. In alternative embodiments, different angular positions may be used, such as 65°, 70°, 75°, 105°, 128°, etc. To measure linear stiffness and damping, the pylon is mechanically constrained to be at a set angle. A static load is applied and a force-displacement curve can be determined and used to estimate stiffness. A guided, user-induced (manual) or automated (actuated) oscillation load is used to measure the damping ratio according to oscillation decay. Loading and unloading of the prosthesis or orthosis under a defined loading or displacement rate using the automated system will estimate hysteresis (energy loss) at a given prosthesis or orthosis orientation. For AFO testing, the device can be fixed to a robotic foot with a near-frictionless ankle joint. Analytical and control software is used built to record, store, analyze, and visualize testing data and generate intuitive figures and parameters. Key parameters include roll-over shape, rotational stiffness, linear stiffness, and linear damping, although other parameters can be utilized in other embodiments.

The protocols used have demonstrated high levels of accuracy and precision and are modelled after standardized methods for characterizing prosthesis mechanical properties independent of the user. In one embodiment, the device undergoes cycles of loading to 1230 N and unloading to 100 N at a rate of 200 N/s. Using custom software, the force-displacement curve is used to estimate the linear damping coefficient from the hysteresis loop and linear stiffness (N/mm) through a best fit line to the loading curve. Non-linear models can also be applied to capture the non-linear shape of the force-displacement curve and better model non-linear behavior of prostheses and orthoses during loading and unloading. Estimations of damping and stiffness are averaged over four loading-unloading cycles. The test-retest reliability is assessed by calculating the standard deviation and 95% confidence interval across the four cycles. In alternative embodiments, fewer or additional cycles may be used. For orthosis testing, multiple different prefabricated ankle-foot orthoses can be fixed to a rigid adapter at the proximal end and tested in the same orientation as the prosthesis keel test.

The same four-cycle test protocol can be used to estimate linear stiffness and damping. System validity can be assessed by capturing the same data across four cycles and comparing results to the materials test system data. It is expected that there is no more than a 5% discrepancy between the manual and actuated systems. Data collection for these prostheses and orthoses using the prototypes can be performed by two investigators to assess inter-rater reliability consistent with previous protocols for this assessment of bench tests with a materials test system. Inter-rater reliability will be assessed through estimation of the intraclass correlation coefficient and Bland-Altman plots, and it is expected for values to be equivalent to those estimated for a previous inter-rater reliability assessment.

Figure 7:
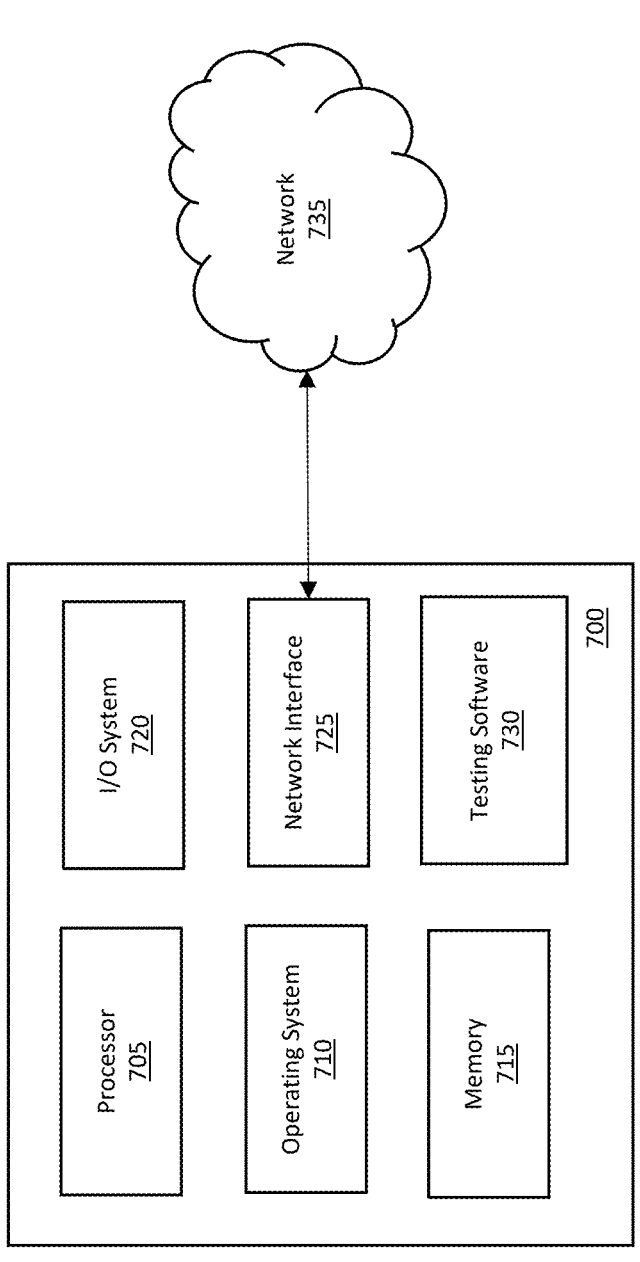
FIG. 7 depicts a computing device in direct or indirect communication with a network in accordance with an illustrative embodiment.

In an illustrative embodiment, the automated version of the proposed system can include a computing device or system that is configured to perform any of the operations described herein. FIG. 7 depicts a computing device 700 in direct or indirect communication with a network 735 in accordance with an illustrative embodiment. In alternative embodiments, the computing device 700 may be in direct communication with another computer (as opposed to networked communication) such as a cell phone, tablet, laptop computer, etc.

The computing device 700 includes a processor 705, an operating system 710, a memory 715, an input/output (I/O) system 720, a network interface 725, and testing software 730. In alternative embodiments, the computing device 700 may include fewer, additional, and/or different components. The components of the computing device 700 communicate with one another via one or more buses or any other interconnect system.

The processor 705 of the computing device 700 can be in electrical communication with and used to control any of the system components described herein, such as actuators, accelerometers, a translatable platform, motors, lead screws, transducers, load cells, etc. The processor 705 can be any type of computer processor known in the art, and can include a plurality of processors and/or a plurality of processing cores. The processor 705 can include a controller, a micro-controller, an audio processor, a graphics processing unit, a hardware accelerator, a digital signal processor, etc. Additionally, the processor 705 may be implemented as a complex instruction set computer processor, a reduced instruction set computer processor, an x86 instruction set computer processor, etc. The processor 705 is used to run the operating system 710, which can be a custom operating system specific to the requirements of the proposed system.

The operating system 710 is stored in the memory 715, which is also used to store programs, prosthetic or orthotic data, patient information, algorithms, network and communications data, peripheral component data, and other operating instructions. The memory 715 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 720, or user interface, is the framework which enables users (and peripheral devices) to interact with the computing device 700. The I/O system 720 can include one or more keys or a keyboard, one or more buttons, one or more displays, a speaker, a microphone, etc. that allow the user to interact with and control the computing device 700. The I/O system 720 also includes circuitry and a bus structure to interface with peripheral computing components such as power sources, sensors, etc.

The network interface 725 includes transceiver circuitry that allows the computing device 700 to transmit and receive data to/from other devices such as user device(s), remote computing systems, servers, websites, etc. The network interface 725 enables communication through the network 735, which can be one or more communication networks. The network 735 can include a cable network, a fiber network, a cellular network, a wi-fi network, a landline telephone network, a microwave network, a satellite network, etc. The network interface 725 also includes circuitry to allow device-to-device communication such as near field communication (NFC), Bluetooth® communication, etc.

The testing software 730 can include hardware, software, and algorithms (e.g., in the form of computer-readable instructions) which, upon activation or execution by the processor 705, performs any of the various operations described herein such as orienting a prosthesis/orthosis, applying a load to the prosthesis/orthosis, receiving sensed data, performing analyses of sensed data, generating control signals, processing test result data, performing device comparisons, transmitting test result data for remote processing, etc. The testing software 730 can utilize the processor 705 and/or the memory 715 as discussed above.

The proposed system is the first available tool to characterize the mechanical function of prostheses and orthoses, and to be widely-accessible due to its minimal size and cost. As discussed herein, knowledge of prosthesis and orthosis mechanical function will aid prosthesis and orthosis prescription guidelines for improved patient quality of life, interpretation and design of prostheses and orthoses comparative research studies, and instruction of materials science in clinical and engineering educational courses. As also discussed, the proposed systems are not limited to the testing of prostheses and orthoses. Rather, the proposed systems can also be used to test any type of footwear, such as shoes, sandals, boots, athletic equipment, etc. Using a similar dummy foot for testing orthoses, different footwear can be tested to characterize their relative mechanical properties for the purpose of iterative evaluation and design processes. Similar to AFOs, footwear mechanical properties have an effect on walking and running behavior and this system can be used to quantify those mechanical properties to inform education, research, clinical, and industry practices.

Thus, described herein are methods and systems that provide a universal way to characterize the mechanical function of lower limb prostheses and orthoses in clinics, research, and educational settings. The proposed methods and systems provide the first available tool to characterize the mechanical function of prostheses and orthoses that is widely accessible due to its minimal size and relative cost. One of the major advantages of this system is that the pylon does not constrain the prosthesis deformation. The pylon only applies bodyweight-like load to the prosthesis, and lets the prosthesis deform naturally. The prosthesis is therefore actually under-constrained when fixed in the system and during testing. This contrasts with traditional systems, which typically constrain the deformation of the prosthesis in ways not typically seen when used by people in real world environments.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A prosthesis and orthosis testing system comprising:
a platform that receives a prosthesis or orthosis;
a motor or a weight configured to apply a load to the prosthesis or orthosis through a pylon;
one or more load cells configured to measure a magnitude of the load on the prosthesis or orthosis;
one or more encoders configured to measure one or more positions and one or more orientations of the prosthesis or orthosis in response to the applied load, wherein the one or more encoders are configured to calculate a deformation of the prosthesis or orthosis based on the one or more positions and the one or more orientations of the prosthesis or orthosis, and wherein a characteristic of the prosthesis or orthosis is determined based on the deformation; and a processor in communication with the one or more encoders, wherein the processor is configured to determine a center of pressure location on the prosthesis or orthosis based at least in part on data from the one or more encoders.

2. The system of claim 1, further comprising a linear actuator attached to the platform, wherein the motor is configured to manipulate the linear actuator to move the pylon.

3. The system of claim 1, further comprising an accelerometer configured to measure an acceleration of the prosthesis or orthosis in response to the applied load.

4. The system of claim 1, wherein the one or more load cells comprise an integrated 3-axis load cell.

5. The system of claim 1, wherein the one or more encoders comprise one or more linear encoders and one or more rotational encoders.

6. The system of claim 1, wherein the pylon is attached to the platform, and wherein the prosthesis or orthosis is mounted to the pylon.

7. The system of claim 1, wherein the processor is configured to determine a roll-over shape of the prosthesis or orthosis based at least in part on the data from the one or more encoders.

8. The system of claim 1, wherein the processor is configured to determine a torque-ankle curve of the prosthesis or orthosis based at least in part on the data from the one or more encoders.

9. The system of claim 1, wherein the motor or the weight moves the pylon through a range of angles under the load.

10. The system of claim 1, wherein the pylon is constrained at a fixed angle such that the load is axially applied to the pylon by the motor or the weight.

* * * * *